(12) United States Patent
Tian et al.

(10) Patent No.: US 7,241,754 B2
(45) Date of Patent: Jul. 10, 2007

(54) 2-DESMETHYL ANSAMYCIN COMPOUNDS

(75) Inventors: Zong-Qiang Tian, Fremont, CA (US); Robert McDaniel, Palo Alto, CA (US); David C. Myles, Kensington, CA (US); Kedar Gautam Patel, Palo Alto, CA (US); Misty Piagentini, Fremont, CA (US); Zhan Wang, El Dorado Hills, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 107 days.

(21) Appl. No.: 10/868,724

(22) Filed: Jun. 14, 2004

(65) Prior Publication Data

US 2005/0026894 A1    Feb. 3, 2005

Related U.S. Application Data

(63) Continuation-in-part of application No. 10/461,194, filed on Jun. 13, 2003.

(60) Provisional application No. 60/535,413, filed on Jan. 8, 2004, provisional application No. 60/528,469, filed on Dec. 9, 2003.

(51) Int. Cl.
- *C07D 225/04* (2006.01)
- *C07D 225/06* (2006.01)
- *A61K 31/395* (2006.01)
- *A61K 31/33* (2006.01)
- *A61K 31/40* (2006.01)

(52) U.S. Cl. ............... 514/183; 514/235.2; 540/461
(58) Field of Classification Search ............... 540/461; 514/183, 235.2
See application file for complete search history.

(56) References Cited

U.S. PATENT DOCUMENTS

| | | | |
|---|---|---|---|
| 3,954,737 A | 5/1976 | Rinehart, Jr. et al. | 260/239.3 P |
| 3,987,035 A | 10/1976 | Rinehart, Jr. et al. | 260/239.3 P |
| 4,261,989 A | 4/1981 | Sasaki et al. | 424/244 |
| 4,421,687 A | 12/1983 | Hasegawa et al. | 260/239.3 B |
| 4,421,688 A | 12/1983 | Muroi et al. | 260/239.3 B |
| 4,540,517 A | 9/1985 | Tanida et al. | 260/239.3 B |
| 5,387,584 A | 2/1995 | Schnur | 514/183 |
| 5,932,566 A | 8/1999 | Schnur et al. | 514/183 |
| 6,015,659 A | 1/2000 | Welch et al. | 435/1.2 |
| 6,682,758 B1 | 1/2004 | Tabibi et al. | 424/450 |
| 2003/0011450 A1 | 1/2003 | Shen | 514/234.5 |
| 2004/0077058 A1 | 4/2004 | Hutchinson et al. | 435/119 |

FOREIGN PATENT DOCUMENTS

| JP | 56-100766 | 8/1981 |
|---|---|---|
| JP | 57-163369 | 10/1982 |
| JP | 63-218620 | 9/1988 |
| JP | 04-46120 | 2/1992 |
| WO | WO 93/14215 A1 | 7/1993 |
| WO | WO 94/08578 A2 | 4/1994 |
| WO | WO 00/03737 A2 | 1/2000 |
| WO | WO 02/36574 A1 | 5/2002 |
| WO | WO 02/079167 A1 | 10/2002 |
| WO | WO 2003/066005 A2 | 8/2003 |
| WO | WO 2003/106653 A2 | 12/2003 |

OTHER PUBLICATIONS

Bierman et al., *Gene* 116, 43-49 (1992), "Plasmid cloning vectors for the conjugal transfer of DNA from *Escherichia coli* to *Streptomyces spp.*"
Carreras et al., *Anal. Biochem.*, 317 (1), 40-46 (Jun. 2003), "Filter Binding Assay for the Geldanamycin-Heat Shock Protein 90 Interaction".
Chemical Abstracts 110:231340 (abstract of JP 63-218620).
Chemical Abstracts 117:63002 (abstract of JP 046120).
DeBoer et al., *J. Antibiotics* 29, 1182-1188 (1976), "The Description and Antibiotic Production of *Streptomyces Hygroscopicus* var. *geldanus*".
Jez et al., *Chemistry & Biology*, 10, 361-368 (2003), "Crystal Structure and Molecular Modeling of 17-DMAG in Complex with Human Hsp90".
McDaniel et al., *Proc. Natl. Acad. Sci. USA*, 96, 1846-1851 (1999), "Multiple Genetic Modifications of the Erythromycin Polyketide Synthase to Produce a Library of Novel 'Unnatural' Natural Products".
Muroi et al., *Tetrahedron* 37, 1123-1130 (1981), "The Structures of Macbecins I and II".
Omura et al., *J. Antibiotics* 37 (10), 1264-1267 (1984), "Chemical Modification and Antitumor Activity of Herbimycin A, 8,9-Epoxide, 7,9-Cyclic Carbamate, and 17- or 19-Amino Derivatives".

(Continued)

*Primary Examiner*—Bruck Kifle
(74) *Attorney, Agent, or Firm*—Yuan Chao

(57) ABSTRACT

2-Desmethyl ansamycins having a structure according to formula I, where $R^1$, $R^2$, $R^3$, $R^4$, $R^5$ and $R^6$ are as defined herein, and other 2-desmethyl ansamycins are useful as antiproliferative agents

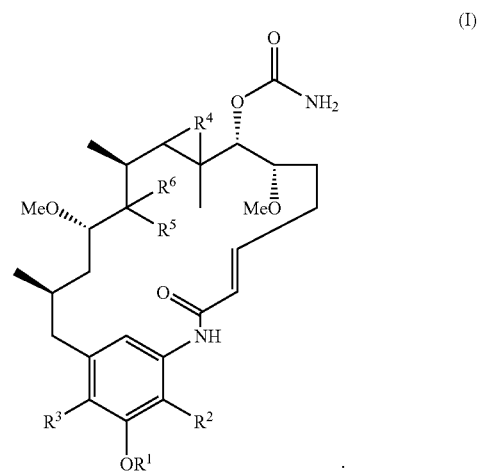

(I)

29 Claims, No Drawings

OTHER PUBLICATIONS

Sasaki et al., *J. Antibiotics* 32 (8), 849-851 (1979), "Growth Inhibition of Virus Transformed Cells in Vitro and Antitumor Activity in Vivo of Geldanamycin and its Derivatives".

Schnur et al., *J. Med. Chem.*, 38, 3806-3812 (1995), "Inhibition of Oncogene Products p. 185 (erbB-2) in Vitro and in Vivo by Geldanamycin and Dihydrogeldanamycin Derivatives".

Schnur et al., *J. Med. Chem.*, 38, 3813-3820 (1995), "erbB-2 Oncogene Inhibition by Geldanamycin Derivatives: Synthesis, Mechanism of Action, and Structure-Activity Relationships".

Shibata et al., *J. Antibiotics* 39 (11), 1630-1633 (1986), "The Structure and Cytocidal Activity of Herbimycin C".

Sreedhar et al., *FEBS Letters*, 562 (1-3), 11-15 (2004), "Hsp90 Isoforms: Functions, Expression and Clinical Importance".

Uehara et al., *J. Antibiotics* 41 (5), 831-834 (1988), "Effects of Herbimycin Derivatives on src Oncogene Function in Relation to Antitumor Activity".

Patel et al., *Chemistry & Biology*, 11, 1625-1633 (2004), "Engineered Biosynthesis of Geldanamycin Analogs for Hsp90 Inhibition".

2-DESMETHYL ANSAMYCIN COMPOUNDS

CROSS-REFERENCE TO RELATED APPLICATIONS

This application (a) is a continuation-in-part of U.S. application Ser. No. 10/461,194, filed Jun. 13, 2003, and (b) claims the benefit of US Provisional Applications Nos. 60/528,469, filed Dec. 9, 2003, and 60/535,413, filed Jan. 8, 2004; the disclosures of which are incorporated by reference.

STATEMENT REGARDING FEDERALLY SPONSORED RESEARCH OR DEVELOPMENT

This invention was made in part with government support under SBIR Grant no. 1 R43 CA/GM96262-01, awarded by the National Institutes of Health, Department of Health and Human Services. The government has certain rights in the invention.

BACKGROUND OF THE INVENTION

1. Field of the Invention

This invention relates to 2-desmethyl ansamycin compounds, methods for their preparation, and their use for treating hyperproliferative diseases, in particular cancer.

2. Description of Related Art

Geldanamycin belongs to the ansamycin family of natural products, whose members are characterized by a benzenoid nucleus (typically a benzoquinone or hydroquinone nucleus) connected at two meta positions to form a macrocyclic lactam. Besides geldanamycin, the ansamycins include the macbecins, the herbimycins, the TAN-420s, and reblastatin:

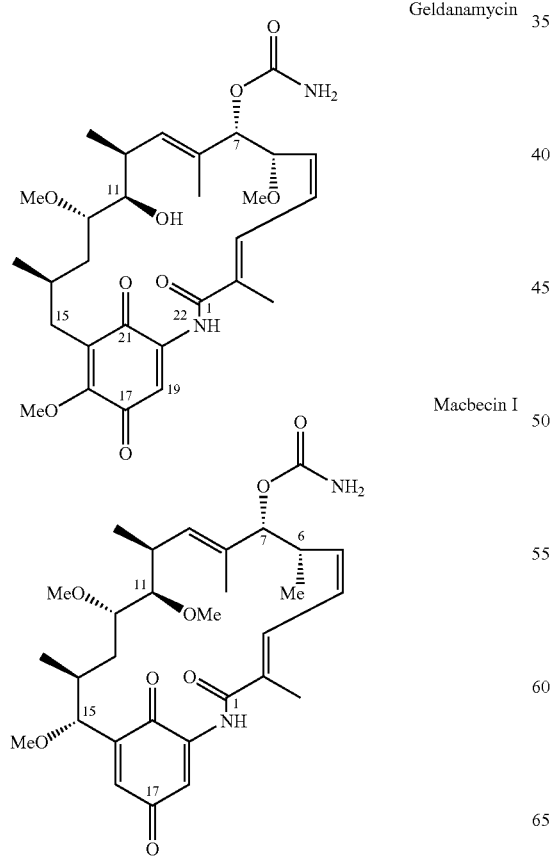

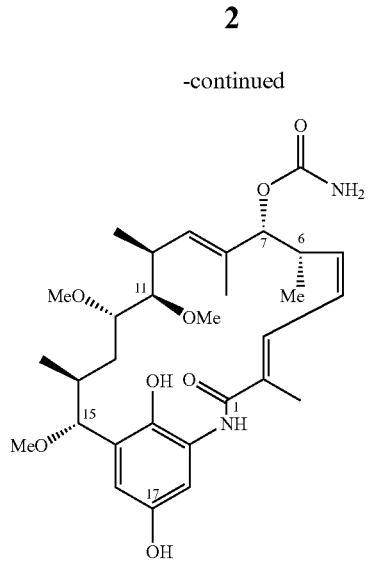

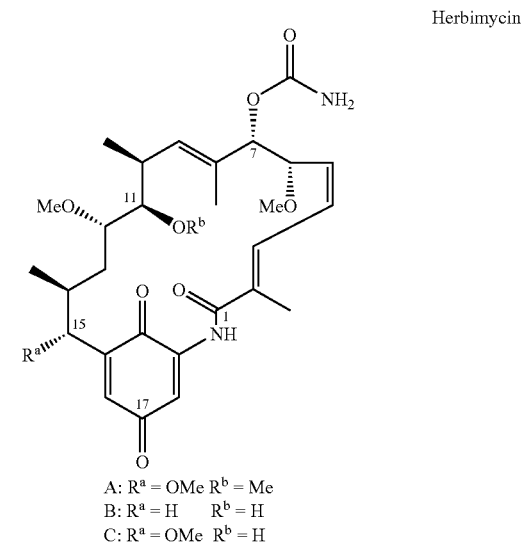

A: $R^a$ = OMe  $R^b$ = Me
B: $R^a$ = H      $R^b$ = H
C: $R^a$ = OMe  $R^b$ = H

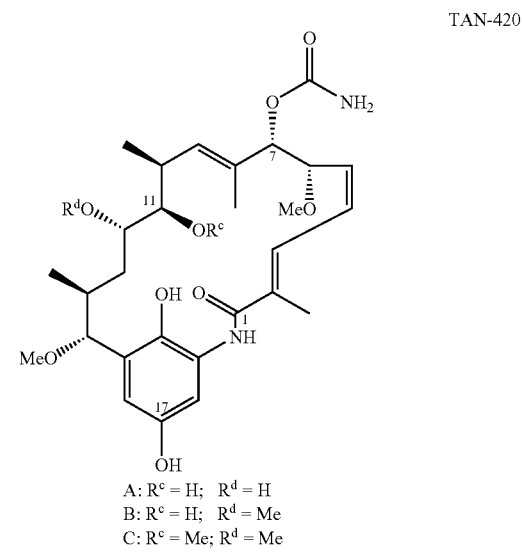

A: $R^c$ = H;   $R^d$ = H
B: $R^c$ = H;   $R^d$ = Me
C: $R^c$ = Me; $R^d$ = Me

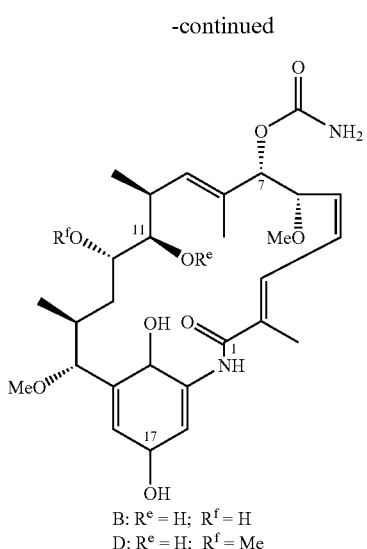

TAN-420

B: $R^e$ = H; $R^f$ = H
D: $R^e$ = H; $R^f$ = Me

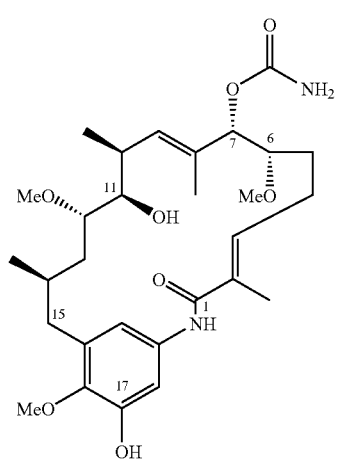

Reblastatin

Geldanamycin and its derivatives are the most extensively studied of the ansamycins. Although geldanamycin was originally identified as a result of screening for antibiotic activity, current interest in it is based primarily on its cytotoxicity towards tumor cells and, therefore, its potential as an anticancer agent. It is an inhibitor of heat shock protein-90 ("Hsp90"), which is involved in the folding, activation and assembly of a wide range of proteins ("client proteins"), including key proteins involved in signal transduction, cell cycle control and transcriptional regulation. The binding of geldanamycin to Hsp90 disrupts Hsp90-client protein interactions, preventing the client proteins from folding correctly and rendering them susceptible to proteasome-mediated destruction. Among the Hsp90 client proteins are many mutated or overexpressed proteins implicated in cancer: p53, Bcr-Abl kinase, Raf-1 kinase, Akt kinase, Npm-Alk kinase p185$^{ErbB2}$ transmembrane kinase, Cdk4, Cdk6, Wee1 (a cell cycle-dependent kinase), HER2/Neu (ErbB2), and hypoxia inducible factor-1α (HIF-1α). However, the hepatotoxicity and poor bioavailability of geldanamycin have lead to its discontinuation as a clinical candidate.

Nevertheless, interest persists in the development of geldanamycin derivatives or analogs (collectively "geldanamycin compounds") having geldanamycin-like bioactivity, but with a better overall spectrum of properties. Position 17 of geldanamycin has been an attractive focal point, chemically speaking, for the synthesis of geldanamycin compounds because its methoxy group is readily displaced by a nucleophile, providing a convenient entry into 17-substituted-17-desmethoxygeldanamycin compounds. Further, structure-activity relationship (SAR) studies have shown that structurally and sterically diverse 17-substituents can be introduced without destroying antitumor activity. For exemplary disclosures relating to 17-substituted geldanamycin compounds, see Sasaki et al., U.S. Pat. No. 4,261,989 (1981); Schnur et al., U.S. Pat. No. 5,932,566 (1999); Schnur et al., *J. Med. Chem.*, 38, 3806-3812 (1995); Schnur et al., *J. Med. Chem.*, 38,3813-3820 (1995); and Ho et al., WO 00/03737 (2000); the disclosures of which are incorporated by reference. The SAR inferences are supported by the X-ray crystal co-structure of the complex between Hsp90α and a geldanamycin derivative (17-DMAG, v. infra), showing that the 17-substituent projects out from the binding pocket and into the solvent (Jez et al., *Chemistry & Biology*, 10, 361-368 (2003)). (Hsp90 exists in a number of isoforms, with the α-isoform being the most common one. For a review on Hsp90 isoforms, see Sreedhar et al., *FEBS Letters* 562 (1-3), 11-15 (2004). Herein, where a particular isoform is referred to, abbreviations such as "Hsp90α" or "Hsp90β" will be used, with "Hsp90" reserved for Hsp90 generically.) Thus, position 17 is a choice one for the introduction of property-modulating substituents, such as a solubilizing group.

The best-known 17-substituted geldanamycin is 17-allylamino-17-demethoxy-geldanamycin ("17-AAG"), currently undergoing clinical trials. Another noteworthy 17-substituted geldanamycin is 17-(2-dimethylaminoethyl) amino-17-demethoxygeldanamycin ("17-DMAG") (Snader et al., WO 02/079167 A1 (2002), incorporated by reference).

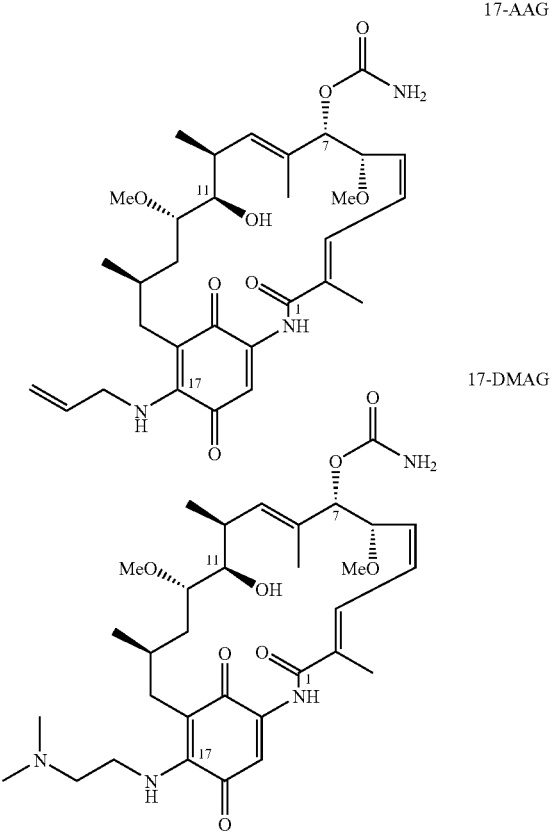

The literature relating to ansamycins wherein the aromatic nucleus is other than a benzoquinone group (e.g., at the hydroquinone or phenol oxidation state) is sparse—not an unexpected outcome considering the benzoquinone group's key role in the activation of the 17-OMe group. There are some disclosures on the isolation of non-benzoquinone natural product congeners such as Macbecin II, TAN-420A, TAN-420B, TAN-420E, and reblastatin. Disclosures of semi-synthetic non-benzoquinone ansamycin derivatives include Rinehart, Jr., et al., U.S. Pat. No. 3,987,035 (1976); Muroi et al., U.S. Pat. No. 4,421,688 (1983); Schnur, U.S. Pat. No. 5,387,584 (1995); Cullen et al., WO 93/14215 A1 (1993); and Sasaki et al., JP 57-163369A (1982); the disclosures of which are incorporated by reference.

BRIEF SUMMARY OF THE INVENTION

This invention provides ansamycin compounds having the aromatic nucleus in a reduced oxidation state relative to the benzoquinone, at the phenol oxidation state. In one embodiment, there is provided a compound having a structure according to formula I

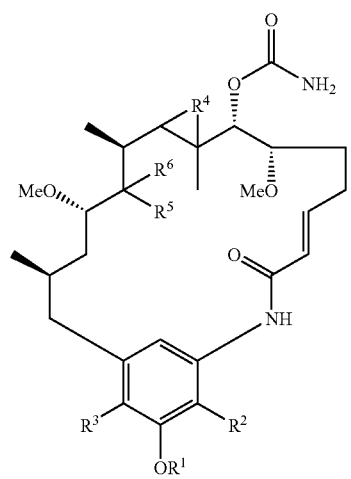

(I)

and the pharmaceutically acceptable solvates, hydrates, salts, esters, and prodrug forms thereof, wherein $R^1$ is H, $C_1$-$C_5$ alkyl, $C_2$-$C_5$ alkenyl, $C_2$-$C_5$ alkynyl, $C_3$-$C_6$ cycloalkyl, $(CH_2)_2C(=O)R^7$, $CH_2C(=O)R^7$, or $C(=O)R^8$;

$R^2$ and $R^3$ are independently H, halogen, $C_1$-$C_5$ alkyl, $C_2$-$C_5$ alkenyl, $C_2$-$C_5$ alkynyl, $C_3$-$C_6$ cycloalkyl, NO, $NO_2$, or $N(R^8R^9)$;

$R^4$ is O or a bond;

$R^5$ is H, $OR^8$, halogen, $OC(=O)R^8$, $O(C=O)N(R^8R^9)$, $OSO_2R^{10}$, or $O(C=O)NHSO_2N(R^8R^9)$;

$R^6$ is H or halogen; or $R^5$ and $R^6$ combine to form =O or =$NOR^8$;

$R^7$ is H, OH, $C_1$-$C_5$ alkyl, $C_2$-$C_5$ alkenyl, $C_2$-$C_5$ alkynyl, $C_3$-$C_6$ cycloalkyl, $OR^8$, or $N(R^8R^9)$;

each $R^8$ is independently H, $C_1$-$C_5$ alkyl, $C_2$-$C_5$ alkenyl, $C_2$-$C_5$ alkynyl, or $C_3$-$C_6$ cycloalkyl;

each $R^9$ is independently H, $C_1$-$C_5$ alkyl, $C_2$-$C_5$ alkenyl, $C_2$-$C_5$ alkynyl, or $C_3$-$C_6$ cycloalkyl; or $R^8$ and $R^9$ form, in combination with a nitrogen atom to which they are commonly attached, a substituted or unsubstituted 3, 4, 5, or 6 membered heterocyclic ring; and $R^{10}$ is $C_1$-$C_5$ alkyl, $C_2$-$C_5$ alkenyl, $C_2$-$C_5$ alkynyl, or $C_3$-$C_6$ cycloalkyl.

In another embodiment, there is provided a compound having a structure according to formula II, where $R^1$, $R^2$, and $R^3$ are as defined hereinabove:

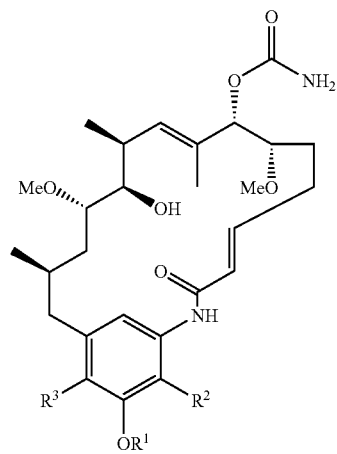

(II)

and the pharmaceutically acceptable solvates, hydrates, salts, esters, and prodrug forms thereof.

In another embodiment, there is provided a compound having a structure according to formula III:

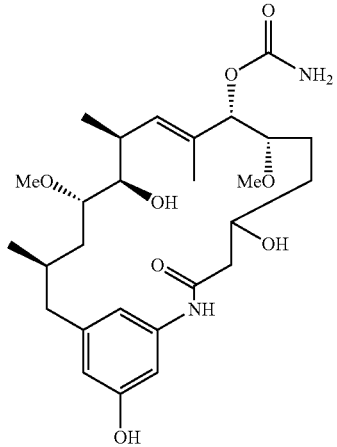

(III)

and the pharmaceutically acceptable solvates, hydrates, salts, esters, and prodrug forms thereof.

In another embodiment, there is provided a compound having a structure according to formula IV:

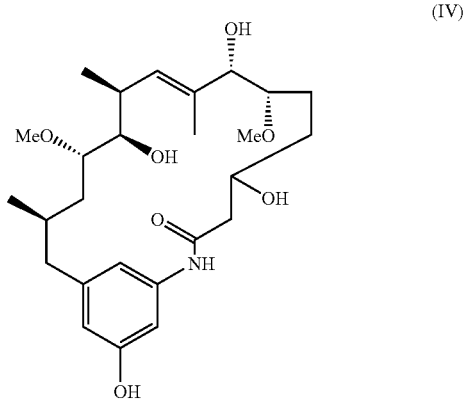

(IV)

and the pharmaceutically acceptable solvates, hydrates, salts, esters, and prodrug forms thereof.

In another embodiment, there is provided a method of treating hyperproliferative disease, comprising administering to a patient suffering from such hyperproliferative disease a therapeutically effective amount of a compound of this invention. The hyperproliferative disease so treated may be cancer, especially breast cancer or leukemia.

In another embodiment, there is provided a pharmaceutical formulation comprising a compound of this invention and an excipient.

DETAILED DESCRIPTION OF THE INVENTION

Definitions

"Alkyl" means an optionally substituted straight or branched chain hydrocarbon moiety having the specified number of carbon atoms in the chain (e.g., as in "$C_1$-$C_8$ alkyl") or, where the number of carbon atoms is not specified, up to 5 carbon atoms in the chain.

"Alkenyl" means an optionally substituted straight or branched chain hydrocarbon moiety having at least one carbon-carbon double bond and the specified number of carbon atoms in the chain (e.g., as in "$C_2$-$C_8$ alkenyl") or, where the number of carbon atoms is not specified, up to 5 carbon atoms in the chain.

"Alkynyl" means an optionally substituted straight or branched chain hydrocarbon moiety having at least one carbon-carbon triple bond and the specified number of carbon atoms in the chain (e.g., as in "$C_2$-$C_8$ alkynyl") or, where the number of carbon atoms is not specified, up to 5 carbon atoms in the chain.

"Alkylaryl," "arylalkyl," "heterocycloalkyl," "alkylheteroaryl," "alkylheterocycle" and the like mean an aryl, heterocyclic, or heteroaryl group, as the case may be, bonded directly to an alkyl moiety, as in benzyl, phenethyl, and the like.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, saturated cyclic hydrocarbon ring system, preferably containing 1 to 3 rings and 3 to 7 carbons per ring (unless a different number of carbons is indicated), which may be further fused with an unsaturated $C_3$-$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen" or "halo" means fluorine, chlorine, bromine and iodine.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quaternized.

Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazo-lidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

Where it is indicated that a group may be substituted, for example by use "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quaternary ammonium, aralkylamino, cycloalkylamino, heterocycloamino, dialkylamino, alkanoylamino, thio, alkylthio, cycloalkylthio, heterocyclothio, ureido, nitro, cyano, carboxy, carboxyalkyl, carbamyl, alkoxycarbonyl, alkylthiono, arylthiono, alkylsulfonyl, sulfonamido, aryloxy, and the like, in addition to those specified herein. The substituent may be further substituted, for example, by halo, hydroxy, alkyl, alkoxy, aryl, substituted aryl, substituted alkyl, substituted aralkyl, and the like. Preferably, the substituent(s) for alkyl, alkenyl, and alkynyl moieties are from one to three in number and are independently selected from N-pyrrolidinyl, N-morpholinyl, N-azetidinyl, hydroxyl, halo, alkoxyl, cyano, amino, alkylamino, and dialkylamino. Preferably, the substituent(s) for aryl, cycloalkyl, and heterocycloalkyl moieties are from one to three in number and are independently selected from alkyl, alkenyl, alkynyl, hydroxyalkyl, haloalkyl, hydroxyl, halo, alkoxyl, cyano, aminoalkyl, alkylaminoalkyl, dialkylaminoalkyl, amino, alkylamino, and dialkylamino.

"Pharmaceutically acceptable ester" means an ester that hydrolyzes in vivo (for example in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Pharmaceutically acceptable salt" means a salt of a compound suitable for pharmaceutical formulation. Suitable pharmaceutically acceptable salts include acid addition salts which may, for example, be formed by mixing a solution of a compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where a compound carries one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in *Design of Prodrugs*, Bundgaard, ed., Elsevier, 1985.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates and hydrates are also encompassed within the scope of this invention.

Compounds and Methods

Geldanamycin is a polyketide, a large family of structurally diverse natural products. The enzymes responsible for the biosynthesis of polyketides are referred to as polyketide synthases (PKSs). Geldanamycin PKS is a Type I (or modular) PKS, characterized by large multifunctional enzymes divided into modules of ketosynthase activity arranged in assembly-line fashion. Each module has a number of enzymatic activities ("domains") that load, activate, and condense a two-carbon (ketide) unit to a growing polyketide chain and may further have modifying domains that chemically alter (reduce, dehydrate, etc.) the just-added ketide unit. The number and order of modules and the types of modifying domains (if any) they contain determine the basic structure of the resulting polyketide.

Initiation of polyketide synthesis occurs at the loading module, comprising an acyltransferase ("AT") and an acyl carrier protein ("ACP") domain, where the first, or starter unit, of the polyketide is loaded onto the PKS, via a high-energy thioester linkage. Subsequent modules ("extender modules") comprising ketosynthase ("KS"), AT, and ACP domains (collectively referred to as the minimal PKS module) load two-carbon malonate based extender units, again via thioester linkages. (The "two-carbon" phraseology refers to the polyketide main chain carbon atoms only; the extender unit also may have carbon atoms destined for side chains, as in the case of a methyl malonyl extender unit.) The loaded extender unit condenses in a Claisen reaction with the growing polyketide chain attached to the loading module or the immediately preceding extender module, as the case may be, extending the polyketide chain by two carbons. If present, modifying domains such as a ketoreductase ("KR") domain, a dehydratase ("DH") domain, an enoylreductase ("ER") domain, and/or a methyltransferase domain operate on the just-added two-carbon unit and modify it. After the action of the last extender module, a release domain—typically a thioesterase or an amidase domain—releases the polyketide from the PKS, usually forming a lactone or lactam in the process. Next, other enzymes (called "tailoring enzymes" or "modification enzymes") may further modify the polyketide, in what are referred to as post-PKS modifications. Tailoring enzymes include oxygenases, glycosyl- and methyltransferases, acyltransferases, halogenases, cyclases, aminotransferases, and hydroxylases.

It is possible to clone a PKS gene from a producing organism and transform a host organism with it, using recombinant DNA techniques. This way, PKS production can be transferred to a host organism that may have more desirable attributes regarding factors such as polyketide titer, ease of culture, absence of undesired side products, etc. In a variant of this technique, the original PKS gene is modified before transformation of the host organism, so that expression of the modified PKS gene leads to a polyketide other than the one produced by the original PKS gene—an "unnatural" natural product, as it were. Among the modifications that can be effected, the one most immediately relevant to the present invention is known as an "AT swap." The specificity of the starter unit or the extender units accepted by a PKS is governed by its AT domain. In an AT swap, the original AT domain is replaced by an AT domain with a different extender unit specificity from another PKS, to produce a hybrid or chimeric PKS. Consequently, the hybrid PKS accepts, at the module where the replacement occurred, a different extender unit and produces an "unnatural" polyketide.

Hutchinson et al., US 2004/0077058 A1 (2004), and WO 03/106653 A2 (2003) (collectively the "Hutchinson applications"), the disclosures of which are incorporated herein by reference, describe the geldanamycin PKS gene cluster and its cloning from the natural producing organism, *Streptomyces hygroscopicus* var. *geldanus* NRRL 3602. Geldanamycin PKS comprises a loading domain accepting 3-amino-5-hydroxybenzoic acid (AHBA) as the starter unit and seven modules each adding an extender unit (malonyl, 2-methoxymalonyl, or 2-methylmalonyl, depending on the module). The initial product of the geldanamycin PKS is progeldanamycin, which is converted to geldanamycin by the action of tailoring enzymes: carbamoylation of the C7 hydroxyl group; hydroxylation of C17 and O-methylation of the hydroxyl group so introduced; oxidation of C21; and oxidation to introduce the C4-C5 double bond:

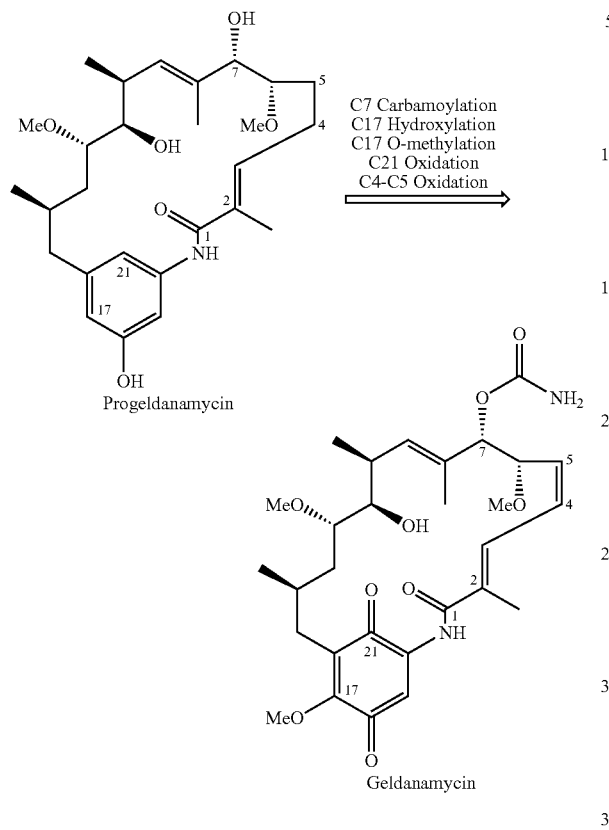

The seventh module AT domain of geldanamycin PKS ("gdmAT7") specifies a 2-methylmalonyl extender unit, the precursor to C1 and C2 and the pendant C2-Me of progeldanamycin. As described in the Hutchinson applications and in Example 1 hereinbelow, an AT swap can be performed in which gdmAT7 is replaced by the AT domain of the second module of rapamycin PKS ("rapAT2"), which specifies a malonyl extender unit. The expression of the hybrid PKS resulting from this gdmAT7→rapAT2 swap theoretically leads to 2-desmethylpro-geldanamycin (not isolated). After tailoring, compound 1-A was isolated, along with compounds III and IV.

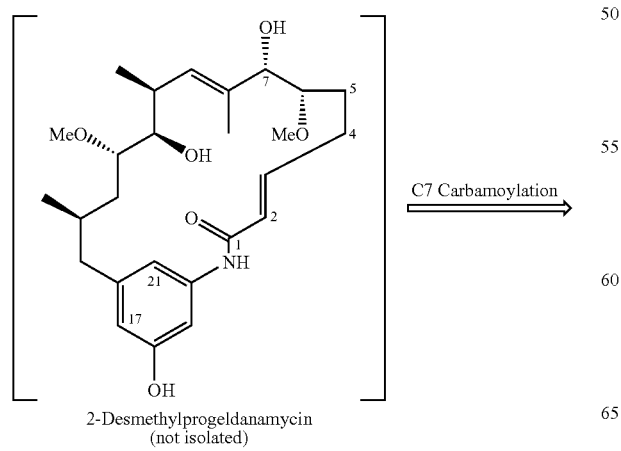

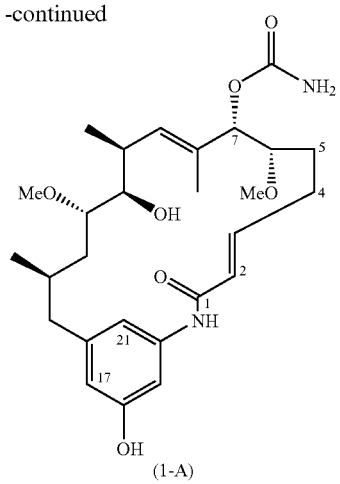

The isolation of compounds 1-A, III, and IV means that, unexpectedly, 2-des-methylprogeldanamycin did not undergo the same suite of tailoring steps that progeldanamycin did. Instead, it underwent some tailoring steps not undergone by progeldanamycin, and vice-versa. Chemical modification of compound 1-A provided other compounds of formula I or II.

Turning now to the R-groups ($R^1$, $R^2$, etc.) of formulae I and II, which are reproduced below for convenience, various preferred embodiments are disclosed. Where an R-group occurs in both formulae, as in the case of $R^1$, $R^2$, and $R^3$, a disclosure applies to both formulae unless the context clearly indicates otherwise. Where an R-group occurs only in formula I, as in the case of $R^4$, $R^5$, and $R^6$, a disclosure applies only to formula I.

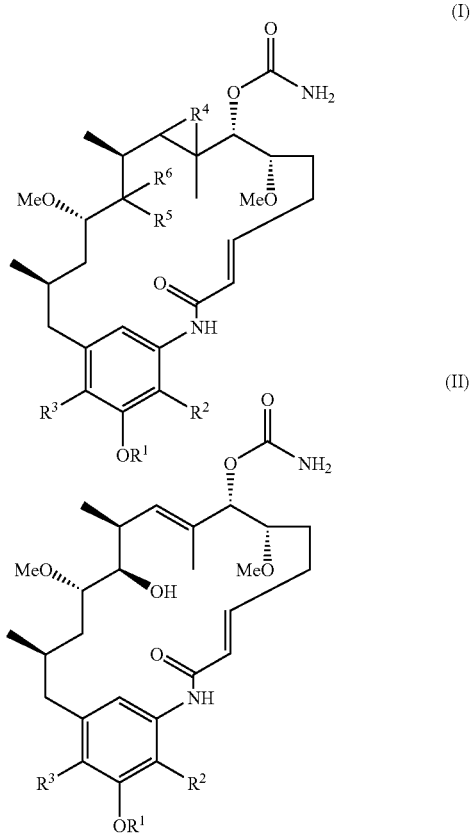

In one preferred embodiment, each of $R^2$ and $R^3$ is H and $R^1$ is other than H (but otherwise as defined in the BRIEF SUMMARY OF THE INVENTION section, above).

In another preferred embodiment, Ris H and at least one of $R^2$ and $R^3$ is other than H (but otherwise as defined in the BRIEF SUMMARY OF THE INVENTION section, above).

In another preferred embodiment, $R^4$ is a bond; $R^5$ is halogen (preferably fluoro); $R^6$ is H; and $R^1$, $R^2$, and $R^3$ are as defined in the BRIEF SUMMARY OF THE INVENTION section, above.

In another preferred embodiment, $R^4$ is a bond; $R^5$ and $R^6$ combine to form =O or =NOR$^8$; and $R^1$, $R^2$, $R^3$, and $R^8$ are as defined in the BRIEF SUMMARY OF THE INVENTION section, above. Preferably, where $R^5$ and $R^6$ combine to form an oxime group =NOR$^8$, $R^8$ is H.

In another preferred embodiment, $R^4$ is a bond and $R^1$, $R^2$, $R^3$, $R^5$ and $R^6$ are as defined in the BRIEF SUMMARY OF THE INVENTION section, above.

In another preferred embodiment, $R^4$ is O; $R^5$ is OH; $R^6$ is H; and $R^1$, $R^2$, and $R^3$, are as defined in the BRIEF SUMMARY OF THE INVENTION section, above.

For the sake of avoiding any misunderstanding, when it is stated that $R^4$ is a bond or that $R^4$ is O, the following structures are intended, respectively:

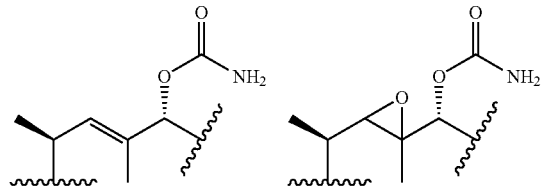

Preferably, $R^1$ is H, $C_1$-$C_5$ alkyl, $C_2$-$C_5$ alkenyl, or $CH_2C$(=O)$R^7$, where $R^7$ is as defined in the BRIEF SUMMARY OF THE INVENTION section, above.

In an embodiment where $R^1$ is other than H, it preferably is $C_1$-$C_5$ alkyl, $C_2$-$C_5$ alkenyl, or $CH_2C$(=O)$R^7$ and more preferably is

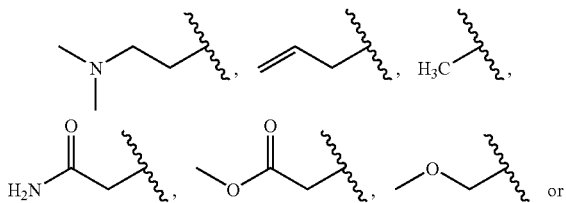

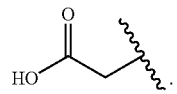

In another preferred embodiment, at least one of $R^2$ and $R^3$ is halogen (especially Br) or an amino-substituted methylene group. Preferably, the latter group is

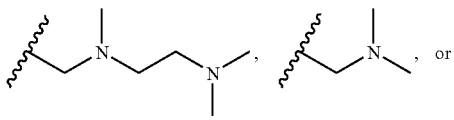

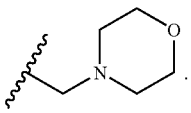

In one variant, $R^2$ and $R^3$ are the same, preferably both being Br. In another variant, one of $R^2$ and $R^3$ is H and the other is halogen or an amino-substituted methylene group.

In another preferred embodiment, $R^4$ is a bond; $R^5$ is OH, fluoro, or OMe; $R^6$ is H; and $R^1$, $R^2$, and $R^3$ are as defined in the BRIEF SUMMARY OF THE INVENTION section above. More preferably, $R^5$ is OH or OMe.

In formula I, $R^5$ and $R^6$ preferably are disposed according to the following absolute stereochemistry:

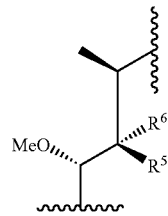

Specific examples of compounds according to formula II are shown in Table 1, where $R^1$, $R^2$, and $R^3$ are selected from the combinations set forth therein.

TABLE 1

| Ref. | $R^1$ | $R^2$ | $R^3$ |
|---|---|---|---|
| 1-A | H | H | H |
| 1-B | 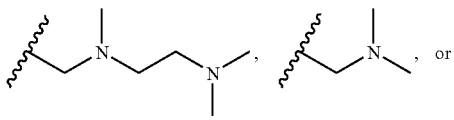 | H | H |
| 1-C | 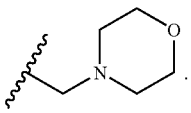 | H | H |

TABLE 1-continued

| Ref. | R¹ | R² | R³ |
|---|---|---|---|
| 1-D | Me | H | H |
| 1-E | 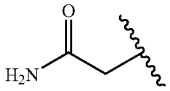 | H | H |
| 1-F | H | 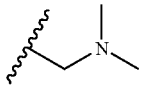 | H |
| 1-G | H | 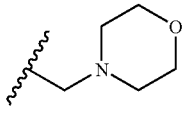 | H |
| 1-H | 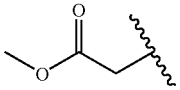 | H | H |
| 1-I | 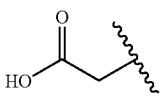 | H | H |
| 1-J | H | Br | H |
| 1-K | H | H | Br |
| 1-L | 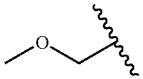 | H | H |
| 1-M | H | Br | Br |
| 1-N | H | Br | 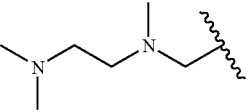 |
| 1-O | H | 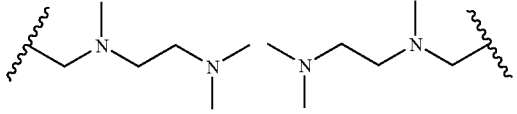 | 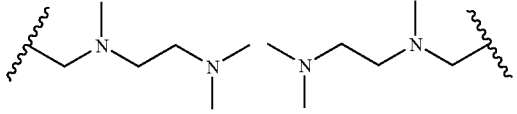 |
| 1-P | H | 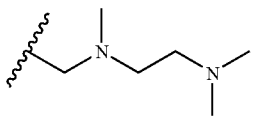 | H |

As noted above, compound 1-A can be converted to other compounds of this invention. Some exemplary conversions are discussed below.

18-O-Ether compounds of formula I or II—i.e., compounds where R¹ is other than H—can be prepared as shown in Procedure A. (For the sake of convenience and brevity, partial chemical structures are used in illustrating this and other synthetic procedures.) Compound 1-A is heated in the presence of a base in a suitable solvent and an alkylating agent R$^g$X, where R$^g$ is an alkyl, alkenyl, cycloalkyl, etc., group and X is a leaving group such as chloride, bromide, iodide, and the like. In some instances, a di-alkylated side-product resulting from reaction at both the 18-OH and 22-N positions was also obtained.

Procedure A

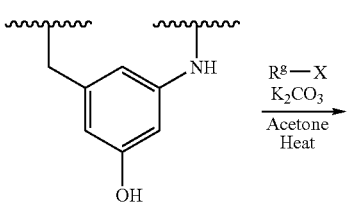

-continued

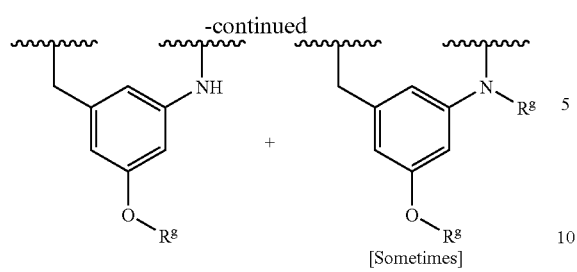

[Sometimes]

Compounds according to formula I or II having an aminomethyl group at position 19 can be prepared by a Mannich reaction, as illustrated in Procedure B. Compound 1-A is reacted with an amine $R^hR^iNH$ in the presence of aqueous formaldehyde in an organic solvent. (In $R^hR^iNH$, $R^h$ and $R^i$ are independently alkyl, alkenyl, alkynyl, or cycloalkyl, or combine with the N to form a 3, 4, 5, or 6 member heterocyclic ring.) The aminomethyl group can then be converted to a methyl group by catalytic hydrogenation, if desired.

Procedure B

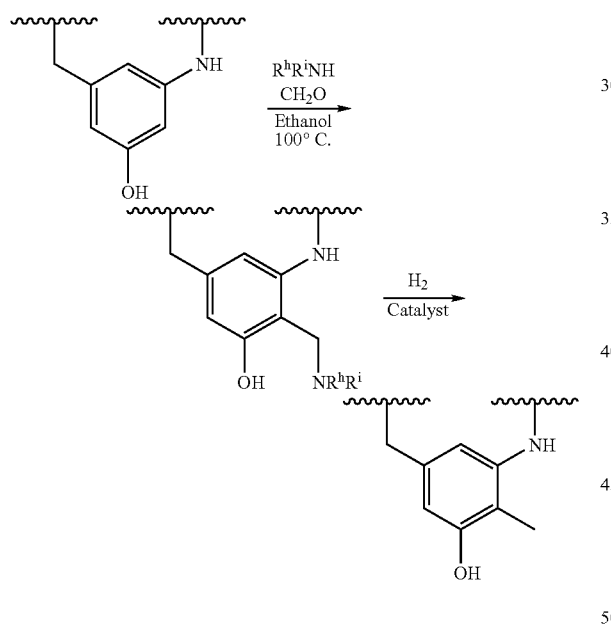

Positions 17 and 19 of the phenol ring of compound 1-A can be halogenated by conventional aromatic halogenation techniques, as illustrated in Procedure C below. A mixture of 17-bromo, 19-bromo, and 17,19-dibromo compounds is obtained.

Procedure C

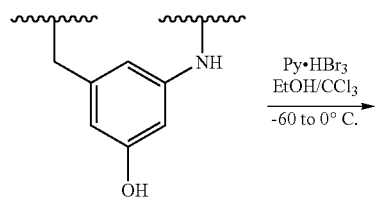

-continued

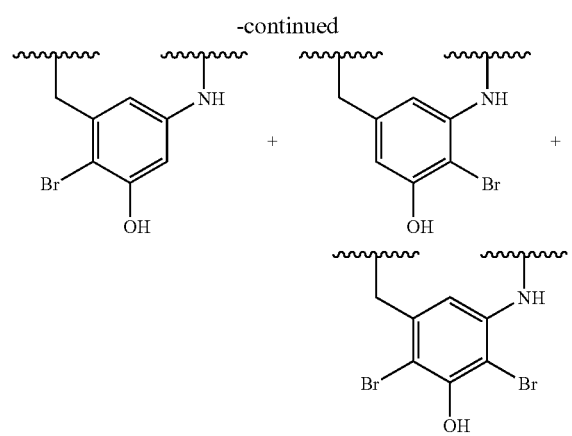

The 19-bromo compound from Procedure C can be converted to the 17-aminomethyl-9-bromo compound via a Mannich reaction as shown in Procedure D. The 19-bromo group can then be reductively removed, if desired.

Procedure D

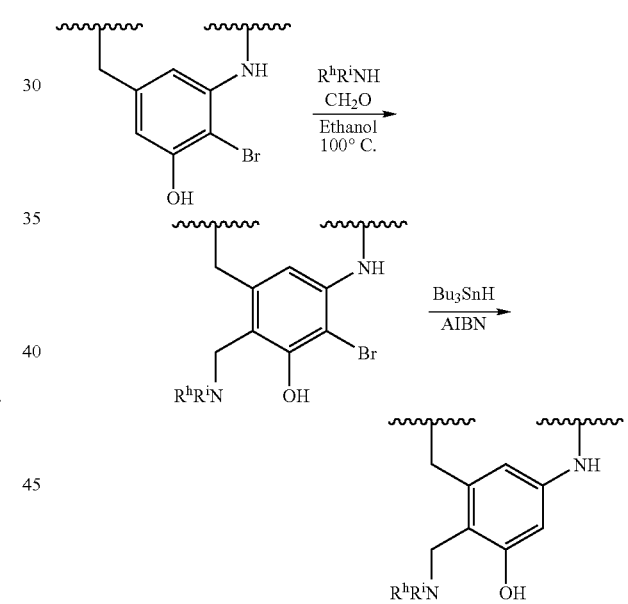

The phenol ring of compound 1-A can be nitrated or nitrosylated as shown in Procedures E and F, respectively. The resulting nitro or nitroso compounds can then be reduced to the corresponding amines.

Procedure E

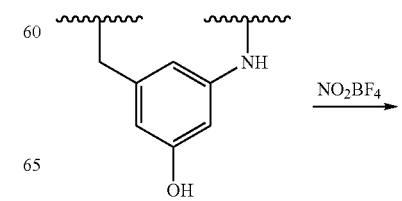

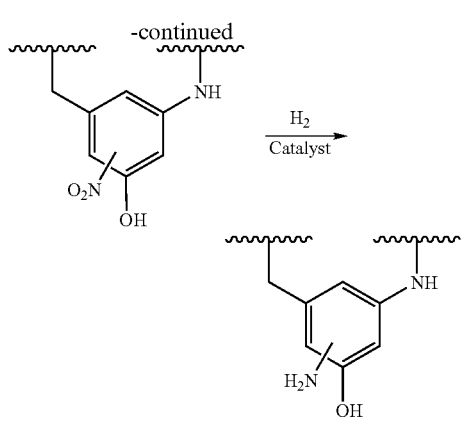

Procedure F

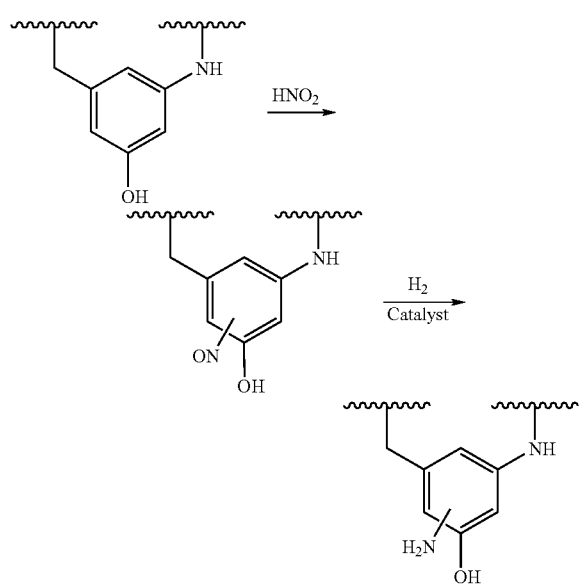

Techniques suitable for the preparation of compounds of formula I by the modification of position 11 are taught in Schnur et al., U.S. Pat. No. 5,932,566 (1999); Santi et al., U.S. Pat. No. 2003/0114450 A1 (2003); Schnur et al., *J Med. Chem.* 38, 3806-3812 (1995); and Schnur et al., *J. Med. Chem.*, 38, 3813-3820 (1995); the disclosures of which are incorporated by reference. Exemplary modifications include: (a) alkylation, acylation, carbamoylation or sulfonylation of the 11-OH group; (b) replacement of the 11-OH group with an epi-11-fluoro group by treatment with diethylaminosulfurtrifluoride (DAST); and (c) oxidation of the 11-OH group to an 11-keto group with Dess-Martin periodinane.

The methylation of the 11-OH group using trimethyloxonium tetrafluoroborate (3 equiv.) and N, N, N, N'-tetramethylnaphthalene-1,8-diamine (1 equiv.) is disclosed in Tian et al., U.S. Pat. No. 6,855,705 B1 (2005); and WO 2005/056531 A1 (2005); the disclosures of which are incorporated herein by reference. Preferably, the procedure is carried out with the 18-OH group protected, for example via a methoxymethyl (MOM) ether, as in compound 1-L.

Compounds in which $R^4$ is O (i.e., 8,9-epoxy compounds) can be prepared by epoxidizing the 8,9 double bond with, for example, m-chloroperbenzoic acid. Exemplary epoxidation conditions are taught in Sasaki et al., U.S. Pat. No. 4,261,989 (1981); Santi et al., U.S. Pat. No. 2003/0114450 A1 (2003); Omura et al., JP 63-218620 (1988); and Omura et al., *J. Antibiotics*, 37 (10), 1264-1267; the disclosures of which are incorporated herein by reference.

17-Bromo compounds can be converted to 17-aryl ones via a Stille or Suzuki coupling reaction.

The present invention also includes methods for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary.

The methods and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved. Thus, the compositions described herein can be combined with other treatment modalities, such as surgery and/or radiation. In some embodiments of the present invention, an agent or procedure is further included to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol.

In another aspect of the present invention, non-cancer disorders that are characterized by cellular hyperproliferation are treated. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis. irritant dermatitis, allergic dermatitis), periodontal disease (i.e., periodontitis), polycystic kidney disease, and type I diabetes. Other examples include vasculitis (e.g., Giant cell arteritis, temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

For human administration, an effective amount of a compound of this invention is used, optionally in combination with a pharmaceutically acceptable carrier. The composition may be dry, or it may be a solution. Treatment may be reactive, for treating an existing condition, or prophylactic, to forestall development of a condition. Compounds of this invention can be used in the preparation of a medicament. The compounds may be administered orally, topically, or parenterally (e.g., intravenously, subcutaneously, intraperitoneally, transdermally).

Preferably, compounds of this invention are provided in a purified and isolated form, for example following column chromatography, high-pressure liquid chromatography, recrystallization, or other purification technique. Where particular stereoisomers of compounds of this invention are denoted, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The practice of this invention can be further understood by reference to the following examples, which are provided by way of illustration and not of limitation.

EXAMPLE 1

*S. hygroscopicus* Strain K309-1

This example describes the substitution of the gdmAT7 domain (which accepts a 2-methymalonyl extender unit) in the geldanamycin PKS with the AT domain the second module of the rapamycin PKS (rapAT2), which accepts a malonyl extender unit, and the transformation of *S. hygroscopicus* with the modified PKS to produce strain K309-1. Strain K309-1 produces compounds 1-A, III, and IV.

Plasmid and delivery vectors were constructed by cloning DNA flanking the AT domains to be substituted in the geldanamycin PKS. The heterologous AT domain used for the substitution was inserted between the flanking fragments and the vector was introduced into the geldanamycin producing organism, *Streptomyces hygroscopicus* NRRL3602. Replacement of the gdmAT7 domain occurs through stepwise double crossing over (homologous recombination).

Two DNA fragments (~1.3 kb) flanking on either side of the AT7 domain were PCR amplified from cosmid pKOS256-107-3 with the following oligonucleotides (EcoRI, BglII, XbaI, BamHI, PstI, HindIII, and NsiI restriction sites are underlined):

```
AT7 Left Flank
for  5'-TTGAATTCAGATCTACGTCACTGCGCGGACAGGAGGTC   [SEQ ID NO:1]

rev  5'-TTTCTAGAGGATCCGCCGTGGGTGGTGGCGTGGCCGGTG  [SEQ ID NO:2]

AT7 Right Flank
for  5'-TTTCTAGACTGCAGCGCGGCGGTCCGGGCGACGTCCGT   [SEQ ID NO:3]

rev  5'-TTAAGCTTATGCATCGGGTCGGTGACCTCGGCGGTGTC   [SEQ ID NO:4]
```

A sample of the cosmid pKOS256-107-3 has been deposited under accession number PTA-4941 with the American Type Culture Collection (ATCC), P.O. Box 1549, Manassas, Va. 20108, USA, according to the terms of the Budapest Treaty on Jan. 16, 2003.

The PCR fragment for the targeted AT was cloned together using XbaI into pUC19 using EcoRI and HindIII restriction sites. The resulting plasmid was pKOS309-8 (AT7 flanks). The rapAT2 cassette (McDaniel et al., 1999, *Proc. Natl. Acad. Sci. U.S.A.* 96, 1846-51) was inserted between the two flanking sequences of the plasmid with BamHI and PstI restriction sites. The AT and flanking fragments were moved into the delivery vector pKC1139 (Bierman et al., 1992, *Gene* 116:43-49) with EcoRI and HindIII restriction sites. The delivery plasmid (pKOS309-23) contained the rapAT2 cassette flanked on either side by 1.3 kb of gdm DNA for homologous recombination into the appropriate module.

The plasmid was introduced in *S. hygroscopicus* NRRL3602 by conjugation using *E. coli* ET12657/pUZ8002 (Kieser et al., Practical *Streptomyces* Genetics: *A Laboratory Manual* (The John Innes Foundation, Norwich, UK, 2000)). Primary exconjugants were first grown in 5 mL liquid R5 containing 100 mg/L apramycin ("apra") at 30° C. for 2 days. To generate the first crossover, 0.2 mL of these cells were used to inoculate 5 mL R5 with apra and grown at 37° C. for 36 hours. This step was repeated once and cells were plated on R5 agar with apra or Tomato agar with apra at 37° C. Single colonies from these plates were grown and their DNA analyzed by Southern hybridization for integration of the delivery plasmid by homologous recombination. Confirmed single crossovers were propagated in R5 without antibiotic selection at 37° C. for ~32 h, plated on Tomato agar plates at 30° C. and allowed to sporulate (~10-14 days). Spores were harvested, plated on R5 and single colonies were screened for sensitivity to apra. To identify second crossovers (AT replacement), apra sensitive colonies were grown in geldanamycin production medium (DeBoer and Dietz, 1976, *J. Antibiot.* 29:1182-8) at 30° C. for 5 days. LC-MS was used to identify production of new geldanamycin compounds. Strain K309-1 containing the gdmAT7 → rapAT2 substitution was found to produce at least three new geldanamycin analogs.

The preparation of *S. hygroscopicus* strain K309-1 is further described in Hutchinson et al., US 2004/0077058 A1 (2004), and in WO 03/106653 A2 (2003), the disclosures of which are incorporated herein by reference.

EXAMPLE 2

Compounds 1-A, III and IV

Cell banks of *S. hygroscopicus* K309-1 were prepared by fermenting in R5 medium at 30° C. for 2-3 days and storing in 30% glycerol at −80° C. Cell banks were used to inoculate seed cultures in R5 and grown to stationary phase (~2-3 days). Production was carried out in 250 mL baffled flasks containing 40 mL of GPM medium and 1.6 g of Amberlite™ XAD resin (Rohm & Haas). The production flasks (50 total) were inoculated with 5% seed each and grown at 30° C. for 4 days. At the end of day 4, the flasks were pooled, centrifuged, and the supernatant decanted without loosing any XAD resin, onto which polyketide product had been adsorbed. To separate cells from the XAD resin, the mixture was re-suspended in water and the XAD resin was allowed to settle. The supernatant with suspended cells was decanted. This procedure was repeated 2-3 times until most of the mycelia was gone. The XAD resin was then filtered using a separation funnel with Whatman™ filter paper and washed briefly with water. The XAD resin was collected and extracted in 100% methanol (~1/10 of total fermentation volume) with stirring for ~30 min. The methanol was decanted and the extraction was repeated 2 more times. The extracts were pooled and concentrated in a rotary evaporator to an aqueous methanolic mixture.

The aqueous methanolic mixture (~50 mL) was further concentrated in a rotary evaporator to remove the methanol and then freeze dried to leave a brown residue. The residue was suspended in methanol (120 mL) and filtered. LC/MS showed the presence of polyketide products in the filtrate. The filtrate was evaporated to dryness, leaving a brown solid (3 g).

Half of the brown solid (1.5 g) was re-dissolved in dichloromethane/methanol. Silica gel (~10 g) was added and the mixture was evaporated to give a free-flowing powder, which was loaded onto a 110 g silica gel column. Chromatograpy was performed using an ISCO Combi-Flash apparatus (detector set at 254 nm), with the following elution profile: 5% methanol in dichloromethane for 36 min; 10% methanol in dichloromethane for 54 min; and 20% methanol in dichloromethane for 36 min. Fractions collected from each solvent composition were combined and analyzed by LC/MS. Compound 1-A and another polyketide were found in the 10% methanol-dichloromethane fractions. The fractions containing compound 1-A (retention time 95-105 min) were combined to give a light yellow solid (~100 mg) after drying, as the largest polyketide component of the product mixture.

The crude product was further purified by HPLC using a C-18 column (MetaChem Polaris 5u C18-A, 150×21.2 mm ID), eluting with a water-acetonitrile gradient. The first pass general gradient was 0 to 100% acetonitrile in water over 30 min at a flow rate of 12 or 16 mL/min. Repurification was effected using a fine elution gradient of 30 to 40% acetonitrile in water over 30 min at a flow rate of 12 or 16 mL/min. The pure fractions were combined and the acetonitrile solvent evaporated. Lyophilization gave pure samples of compound 1-A (~30 mg) and another polyketide (~15 mg, compound III). (A third polyketide (~10 mg, compound IV) could be isolated from crude samples of compound 1-A.)

The analytical data for compound 1-A are: Electrospray ionization time-of-flight mass spectrometry ("ESI TOF MS") m/z 527.2712; calcd for $C_{27}H_{40}N_2O_7Na$ [M+Na]$^+$, 527.2728. $^{13}C$ NMR (DMSO-$d_6$, 100 MHz) δ (relative to DMSO-$d_6$ at 39.5 ppm) 11.2, 17.7, 19.2, 26.1, 27.9, 31.6, 32.9, 34.7, 42.9, 56, 58.4, 72.4, 78.5, 81.2, 81.8, 108.3, 114.3, 118, 122.2, 129.4, 134.2, 138.6, 142.2, 143.7, 156, 157.7, 165.9.

The analytical data for compound III are: ESI TOF MS m/z 545.2831, calcd for $C_{27}H_{42}N_2O_8Na$ ([M+Na]$^+$) 545.2833. $^{13}C$ NMR (DMSO-$d_6$, 100 MHz) δ (relative to DMSO-d6 at 39.5 ppm) 12.6, 16.3, 21, 25, 31.9, 32.7, 33.7, 34.4, 42.6, 45.5, 56.1, 57, 67.4, 73.3, 76.9, 79, 81.7, 104.8, 112, 112.7, 130.3, 130.5, 139.2, 142.7, 156.4, 157, 168.9.

The analytical data for compound IV are ESI TOF MS m/z 502.2783, calcd for $C_{26}H_{41}NO_7Na$ ([M+Na]$^+$) 502.2775. $^{13}C$ NMR (DMSO-d6, 100 MHz) δ (relative to DMSO-$d_6$ at 39.5 ppm) 12.3, 16.5, 20.7, 24.8, 31.6, 32.1, 33.7, 34.1, 42.8, 45.7, 56.2, 57.1, 67.7, 73.6, 75.3, 80.9, 81.4, 104.6, 11.6, 112, 128.8, 133.8, 139.4, 142.4, 157.1, 169.

EXAMPLE 3

Procedure A

18-O-ether compounds were prepared according to Procedure A using the following general protocol: To a solution of compound 1-A (1 equiv.) in dry acetone (~10 mmol/L) was added potassium carbonate powder (3 equiv.) and an alkyl halide (2 equiv.). The mixture was heated to 60° C. and stirred for 16 h (or until all starting material was consumed). The mixture was concentrated on a rotary evaporator, resuspended in ethyl acetate, washed sequentially with water, saturated sodium bicarbonate (aq.), and saturated sodium chloride (aq.). The organic phase was dried over anhydrous sodium sulfate, filtered, and evaporated to dryness. The crude product was purified by reversed phase HPLC, eluted using a gradient of water/acetonitrile. The 18-O-alkyl ether analogs were obtained as white solids. The 18-O, 22-N-dialkyl analogs were isolated in several cases.

The following compounds were made according to the above procedure, with the halide used identified parenthetically.

Compound 1-B (allyl bromide).

ESI TOF MS m/z 567.3020, calcd for $C_{30}H_{44}N_2O_7Na$ ([M+Na]$^+$), 567.3041. $^{13}C$ NMR (CDCl$_3$, 100 MHz) δ (relative to CDCl$_3$ at 77.0 ppm) 11.3, 17.8, 18.7, 26.3, 27.8, 30.6, 32.6, 34.6, 43.2, 56.8, 59.4, 49, 73.3, 78.5, 81.3, 83, 108.5, 115.1, 117.9, 120.9, 121.3, 129.7, 132.9, 133.8, 137.5, 142.4, 145.3, 155.8, 159.1, 167.4. Some the dialkylated product was isolated as a side product.

Compound 1-C (N,N-dimethyl-2-chloroethylammonium chloride).

ESI TOF MS m/z 576.3627, calcd for $C_{31}H_{50}N_3O_7$ ([M+H]$^+$), 576.3643. $^{13}$C NMR (CDCl$_3$, 100 MHz) δ (relative to CDCl$_3$ at 77.0 ppm) 11.3, 17.8, 18.8, 21.9, 26.3, 27.8, 30.8, 32.7, 34.7, 43.1, 44.8, 56.7, 57.2, 59.4, 65.2, 73.2, 78.5, 81.4, 82.9, 108, 114.9, 120.9, 121.2, 129.6, 133.9, 137.7, 142.4, 145.4, 156.2, 158.9, 167.8, 175.9. Compound 1-C was isolated as its acetate salt.

Compound 1-D (methyl iodide).

ESI TOF MS m/z 541.2892, calcd for $C_{28}H_{42}N_2O_7Na$ ([M+Na]$^+$), 541.2884. $^{13}$C NMR (CDCl$_3$, 100 MHz) δ (relative to CDCl$_3$ at 77.0 ppm) 11.2, 17.8, 18.7, 26.2, 27.7, 30.7, 32.6, 34.6, 43.1, 55.4, 56.7, 59.3, 73.2, 78.5, 81.4, 83, 107.5, 114.4, 121, 129.6, 133.8, 137.7, 142.3, 145.1, 156.1, 160, 167.6.

Compound 1-E (2-bromo acetamide).

ESI TOF MS m/z 584.2932, calcd for $C_{29}H_{43}N_3O_8Na$ ([M+Na]$^+$), 584.2942. $^{13}$C NMR (CDCl$_3$ (+10% CD$_3$OD), 100 MHz) δ (relative to CDCl$_3$ at 77.0 ppm) 11.1, 17.4, 18.8, 26.4, 27.7, 30.8, 32.6, 34.6, 43, 56.5, 59, 66.8, 73.1, 78.6, 81.5, 82.5, 107.6, 114.8, 120.7, 121, 129.5, 133.9, 137.9, 142.9, 145.6, 156.6, 157.5, 167.7, 171.5. Some dialkylated product was obtained as a side product.

Compound 1-L (chloromethyl methyl ether).

ESI TOF MS m/z 571.2995, calcd for $C_{29}H_{44}N_2O_8Na$ ([M+Na]$^+$), 571.2990. $^{13}$C NMR (CDCl$_3$, 100 MHz) δ (relative to CDCl$_3$ at 77.0 ppm) 11.2, 17.8, 18.6, 26.2, 27.6, 30.5, 32.5, 34.6, 43, 56, 56.7, 59.4, 73.2, 78.4, 81.3, 82.9, 94.3, 109.8, 116.4, 120.9, 122.1, 129.6, 133.8, 137.6, 142.2, 145.2, 156.2, 157.6, 167.5.

Compound 1-H (methyl 2-bromoacetate).

ESI TOF MS m/z 599.2937, calcd for $C_{30}H_{44}N_2O_9Na$ ([M+Na]$^+$), 599.2939. $^{13}$C NMR (CDCl$_3$, 100 MHz) δ (relative to CDCl$_3$ at 77.0 ppm) 11.3, 17.8, 18.7, 26.3, 27.7, 30.8, 32.6, 34.5, 43.1, 52.3, 56.7, 59.3, 65.1, 73.2, 78.5, 81.4, 82.9, 108.3, 114.3, 121, 121.7, 129.7, 133.8, 137.9, 142.5, 145.4, 156.1, 158.1, 167.5, 169. Some dialkylated product was obtained as a side product.

Compound 1-I was prepared by stirring compound 1-H in potassium carbonate (5 equiv.) in 3:1 (v/v) methanol:water for 20 h at room temperature. The crude product was purified by reversed phase HPLC, eluted using a gradient of water/acetonitrile. ESI TOF MS m/z 585.2803, calcd for $C_{29}H_{42}N_2O_9Na$ ([M+Na]$^+$), 585.2783. $^{13}$C NMR (CD$_3$OD, 100 MHz) δ (relative to CD$_3$OD at 49.0 ppm) 11.8, 18.1, 19.6, 27.5, 29.6, 32.8, 34.1, 36.3, 44.3, 56.9, 60.2, 66.7, 74.5, 80.2, 83.2, 84.5, 109.3, 116.1, 122.1, 122.7, 131.1, 135.8, 139.3, 143.9, 146.4, 159, 160.4, 169.5, 175.4.

EXAMPLE 4

Procedure B

19-Aminomethyl compounds were prepared according to Procedure B using the following general protocol: To a solution of compound 1-A (1 equiv.) in ethanol (~20 mmol/L) was added 37% aqueous formaldehyde (3 equiv.) and a secondary amine (3 equiv.). The mixture was heated to 100° C. for 2 h (or until all starting material was consumed). The mixture was concentrated under vacuum. The residue was re-suspended in ethyl acetate, washed sequentially with water, saturated sodium bicarbonate (aq.), and saturated sodium chloride (aq.). The organic solution was dried over anhydrous sodium sulfate, filtered, and evaporated to dryness. The crude product was purified by reversed phase HPLC, eluted using a gradient of water/acetonitrile.

The following compounds were made according to the preceding general procedure, with the secondary amine identified parenthetically.

Compound 1-F (dimethylamine. 2M in tetrahydrofuran).

ESI TOF MS m/z 562.3497, calcd for $C_{30}H_{48}N_3O_7$ ([M+H]$^+$), 562.3487. $^{13}$C NMR (CDCl$_3$, 100 MHz) δ (relative to CDCl$_3$ at 77 ppm) 11.3, 17.8, 18.6, 26.5, 27.7, 30.4, 32.5, 34.6, 42.8, 44.1, 56.3, 56.8, 59.1, 73.3, 78.7, 81.3, 82.6, 114.4, 117.3, 120.2, 121.1, 129.3, 134.1, 134.8, 141.2, 145.9, 156.4, 158.8, 168.5.

Compound 1-G (morpholine).

ESI TOF MS m/z 604.3594, calcd for $C_{32}H_{50}N_3O_8$ ([M+H]), 604.3592. $^{13}$C NMR (CDCl$_3$, 100 MHz) δ (relative to CDCl$_3$ at 77 ppm) 11.3, 17.7, 18.6, 26.5, 27.8, 30.5, 32.5, 34.6, 42.8, 52.6, 55.7, 56.7, 59.1, 66.6, 73.2, 78.8, 81.3, 82.4, 113.6, 117.1, 120.3, 121.4, 129.2, 134, 135.2, 141.1, 145.7, 156.3, 158.2, 168.5.

Compounds 1-O and 1-P (N,N,N'-trimethylethylenediamine).

A mixture of compounds 1-O and 1-P was obtained, which were then separated. Compound 1-O: $^{13}$C NMR (CDCl$_3$, 100 MHz) δ (relative to CDCl$_3$ at 77.0 ppm) 12.2, 18.0, 19.6, 28.2, 29.4, 32.1, 34.5, 34.9, 40.6, 41.5, 42.1, 45.4, 45.6, 50.9, 54.3, 54.6, 56.4, 56.7, 56.9, 57.0, 58.6, 73.5, 80.4, 80.4, 82.0, 115.0, 116.6, 124.3, 124.3, 129.9, 133.0, 137.8, 138.7, 143.8, 155.9, 157.4, 167.0. ESI TOF MS m/z 733.5225, calcd for $C_{39}H_{69}N_6O_7$ ([M+H]$^+$) 733.5222. Compound 1-P: $^{13}$C NMR (CDCl$_3$, 100 MHz) δ (relative to CDCl$_3$ at 77.0 ppm) 11.3, 17.8, 18.8, 26.5, 27.8, 29.7, 30.8, 32.7, 41.9, 42.9, 45.1, 52.7, 52.9, 55.3, 56.8, 59.2, 73.3, 78.7, 81.5, 82.8, 115.3, 117.2, 120.7, 120.7, 129.5, 134.1, 135.3, 141.0, 145.2, 155.9, 158.5, 167.6. ESI TOF MS m/z 619.4079, calcd for $C_{33}H_{55}N_4O_7$ ([M+H]$^+$) 619.4065.

EXAMPLE 5

Procedure C

Compound 1-A was brominated as follows: To a solution of compound 1-A (20 mg, 0.04 mmol) in ethanol (1 mL) and chloroform (1 mL) cooled at 0° C. was added pyridinium hydrobromide perbromide (16 mg, 0.05 mmol). The orange starting material dissolved in a few minutes, with TLC showing no starting material left. The mixture was concentrated on a rotary evaporator, re-suspended in ethyl acetate, washed sequentially with water, saturated sodium bicarbonate (aq.), and saturated sodium chloride (aq.). The organic phase was dried over anhydrous sodium sulfate, filtered, and evaporated to dryness. The crude product was purified by reverse phase HPLC, eluted using a gradient of water/acetonitrile. Compounds 1-J, 1-K, and 1-M were obtained as white solids, with the yield indicated parenthetically.

Compound 1-J (1.5 mg).

ESI TOF MS m/z 605.1813, calcd for $C_{27}H_{39}BrN_2O_7Na$ ([M+Na]$^+$), 605.1833. $^{13}$C NMR (DMSO-d$_6$, 100 MHz) δ (relative to DMSO-d$_6$ at 39.5 ppm) 10.9, 17.8, 18.1, 25.8, 27.3, 30, 32.1, 34.5, 42.3, 55.9, 58.4, 72.1, 78.2, 80.7, 82.3, 106.3, 116.2, 121, 121.2, 129.1, 134, 137, 139.7, 143.8, 155.9, 165.6.

Compound 1-K (6.6 mg).

ESI TOF MS m/z 605.1846, calcd for $C_{27}H_{39}BrN_2O_7Na$ ([M+Na]$^+$), 605.1833. $^{13}$C NMR (DMSO-d6, 100 MHz) δ (relative to DMSO-$d_6$ at 39.5 ppm) 11.6, 17.2, 20, 27.2, 28.9, 32.2, 34.1, 34.6, 42.7, 55.9, 58.1, 72.8, 79.3, 80.2, 82.2, 108.4, 108.9, 118.1, 122.7, 129.3, 134, 137.3, 141.8, 144.4, 155.1, 156, 165.6.

Compound 1-M (4 mg).

ESI TOF MS m/z 683.0937, calcd for $C_{27}H_{38}Br_2N_2O_7Na$ ([M+Na]$^+$), 683.0938. $^{13}$C NMR (acetone-$d_6$, 100 MHz) δ (relative to acetone-$d_6$ at 29.8 ppm) 12, 17.7, 20.2, 28.3, 30.2, 32.8, 34.7, 35.7, 43.7, 56.7, 59.3, 74.2, 80.7, 82.2, 83, 106.7, 112, 122.6, 130.7, 134.8, 137.2, 141.9, 146.4, 153, 156.8, 166.4.

EXAMPLE 6

Procedure D

To a solution of compound 1-J (12 mg, 0.02 mmol) in ethanol (1 mL) was added 37% aqueous formaldehyde (5 μL, 0.06 mmol) and N,N,N,'-trimethylethylenediamine (8 μL, 0.06 mmol). After heated at 100° C. for 4 h, the mixture was concentrated under vacuum. The residue was re-suspended in ethyl acetate, washed sequentially with water, saturated sodium carbonate (aq.), and saturated sodium chloride (aq.). The organic solution was dried over anhydrous sodium sulfate, filtered, and evaporated to dryness. The crude product was purified by reverse phase HPLC, eluted using a gradient of water/acetonitrile. The product was obtained as a white solid (10 mg). ESI TOF MS m/z 697.3162, calcd for $C_{33}H_{54}BrN_4O_7$ ([M+H]$^+$), 697.3170. $^{13}$C NMR (CDCl$_3$, 100 MHz) δ (relative to CDCl$_3$ at 77 ppm) 12.1, 17.9, 19.4, 28.3, 29.3, 31.7, 34.3, 35, 40.4, 41.5, 45, 53.8, 56.1, 56.3, 56.7, 58.7, 73.5, 80.2, 80.5, 81.7, 103.8, 118.6, 119.7, 122.5, 129.5, 132.9, 135.1, 138.7, 145.7, 156, 156.4, 166.9.

Example 7

Biological Activity

Hsp90 binding was determined according to the procedure of Carreras et al., *Anal. Biochem.*, 317 (1), 40-46 (June 2003), "Filter Binding Assay for the Geldanamycin-Heat Shock Protein 90 Interaction."

Cytotoxicity was determined with SKBr3 cells (ATCC HTB-30), a breast cancer cell line. The SKBr3 cells were maintained in McCoy's 5A modified medium (Invitrogen #16600082) with 10% fetal bovine serum (Hyclone #SH30070.03) and 2mM L-glutamine at 37° C. in a humidified incubator with 5% carbon dioxide atmosphere. Cells were plated into 96-well microtiter back plates at 4,000 cells per 50μL per well, overnight. Serial 10x dilutions of test compound (10 μM to 0.1 pM) in cell culture media were prepared with a Biomek 2000 apparatus, using the protocols of deeper-1000 μL-media and deeper-1000 μL-dilution. 50 μL of each dilution was added to wells containing cells. Each compound or control (medium only) was tested in duplicate. For each assay, the wells contained a final volume of 100 μL (50 μL of cells and 50 μL of compound dilution). After incubating for 72 h, the plates were let stand at room temperature for 30 min. CellTiter-Glo Luminescent Reagent (Promega #G7573) (100 μL) was added to each well. The well contents were mixed for 5 min and the plates were kept at room temperature for another 30 min. Luminescence was recorded using a Wallac VICTOR$^2$ Multilabel Counter (PerkinElmer) and IC$_{50}$ values were determined using Kaleidagraph software (Synergy Software).

Hsp90 binding and cytotoxicity data for compound 1-A through 1-N, together with data for geldanamycin itself, are presented in Table 2.

TABLE 2

| Compound | Hsp90 Binding ($K_d$, nM) | Cytotoxicity against SKBr3 Cells (IC$_{50}$, μM) |
|---|---|---|
| 1-A | 17 | 0.85 |
| 1-B | 1,000 | >5 |
| 1-C | 230 | >10 |
| 1-D | 510 | 6 |
| 1-E | 440 | >5 |
| 1-F | 200 | 0.63 |
| 1-G | 640 | >5 |
| 1-H | 360 | >5 |
| 1-I | 930 | >5 |
| 1-J | 1,700 | >5 |
| 1-K | 140 | 0.80 |
| 1-L | 850 | 1.1 |
| 1-M | 5,900 | >5 |
| 1-N | 31,000 | >5 |
| 1-O | not determined | >5 |
| 1-L | not determined | >5 |
| III | 1,000 | >5 |
| IV | 17,000 | >5 |
| Geldanamycin (comparative) | 500 | 0.023 |

The data show that compounds of this invention exhibit significant Hsp90 binding activity and cytotoxicity towards SKBr3 cells. In a preferred embodiment, compounds of this invention have a $K_d$ for Hsp90 binding of 2,000 nM or less, preferably 1,000 nM or less. In another preferred embodiment, compounds of this invention have an IC$_{50}$ towards SKBr3 cells of 5 μM or less.

Compound 1-A was also evaluated for cytotoxicity against CCFT-CEM cells, a leukemia cell line. Its IC$_{50}$ was 2.5 μM.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A compound having a structure according to formula I

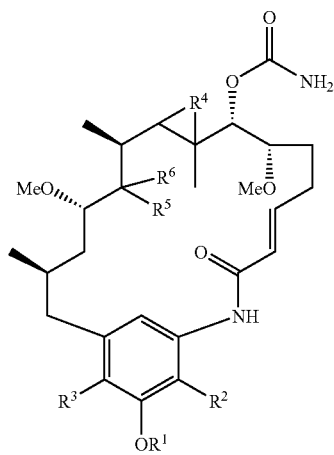

or a pharmaceutically acceptable salt thereof,
wherein
- $R^1$ is H, optionally substituted $C_1$-$C_5$ alkyl, optionally substituted $C_2$-$C_5$ alkenyl, optionally substituted $C_2$-$C_5$ alkynyl, optionally substituted $C_3$-$C_6$ cycloalkyl, $(CH_2)_2C(=O)R^7$, $CH_2C(=O)R^7$, or $C(=O)R^8$;
- $R^2$ and $R^3$ are independently H, halogen, optionally substituted $C_1$-$C_5$ alkyl, optionally substituted $C_2$-$C_5$ alkenyl, optionally substituted $C_2$-$C_5$ alkynyl, optionally substituted $C_3$-$C_6$ cycloalkyl, NO, $NO_2$, or $N(R^8R^9)$;
- $R^4$ is O or a bond;
- $R^5$ is H, $OR^8$, halogen, $OC(=O)R^8$, $O(C=O)N(R^8R^9)$, $OSO2R^{10}$, or $O(C=O)NHSO_2N(R^8R^9)$;
- $R^6$ is H or halogen; or $R^5$ and $R^6$ combine to form =O or =$NOR^8$;
- $R^7$ is H, OH, optionally substituted $C_1$-$C_5$ alkyl, optionally substituted $C_2$-$C_5$ alkenyl, optionally substituted $C_2$-$C_5$ alkynyl, optionally substituted $C_3$-$C_6$ cycloalkyl, $OR^8$, or $N(R^8R^9)$;
- each $R^8$ is independently H, optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl;
- each $R^9$ is independently H, optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl; or $R^8$ and $R^9$ form, in combination with the nitrogen atom to which they are commonly attached, a 3, 4, 5, or 6 membered heterocyclic ring containing 1, 2, or 3 heteroatoms selected from N, O, and S; and
- $R^{10}$ is optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl;

wherein an optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl that is substituted contains a substituent selected from the group consisting of alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino ciuartemary ammonium, aralkylamino, cycloalkylamino, heterocycloamino, dialkylamino, alkanoylamino, thio, alkylthio, cycloalkylthio, heterocyclothio, ureido, nitro, cyano, carboxy, carboxylalkyl, carbamyl, alkoxycarbonyl, alkylthiono, arylthiono, alkylsulfonyl, sulfonamido, and aryloxy.

2. A compound according to claim 1, wherein each of $R^2$ and $R^3$ is H and $R^1$ is other than H.

3. A compound according to claim 1, wherein $R^1$ is H and at least one of $R^2$ and $R^3$ other than H.

4. A compound according to claim 1, wherein $R^4$ is a bond; $R^5$ is OH, fluoro or OMe; and $R^6$ is H.

5. A compound according to claim 1, wherein $R^4$ is a bond and $R^5$ and $R^6$ combine to form =O or =$NOR^8$.

6. A compound according to claim 1, wherein $R^1$ is optionally substituted $C_1$-$C_5$ alkyl, optionally substituted $C_2$-$C_5$ alkenyl, or $CH_2C(=O)R^7$ and each of $R^2$ and $R^3$ is H.

7. A compound according to claim 6, wherein $R^1$ is

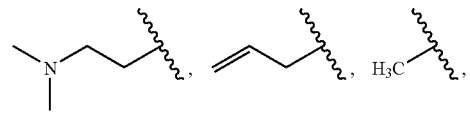

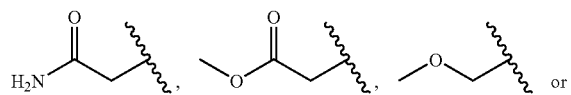

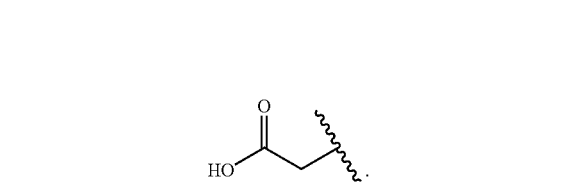

8. A compound according to claim 1, wherein at least one of $R^2$ and $R^3$ is Br or an amino-substituted methylene group.

9. A compound according to claim 8, wherein the amino-substituted methylene group is

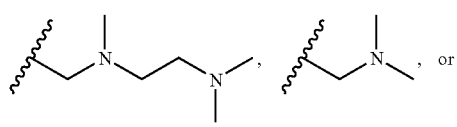

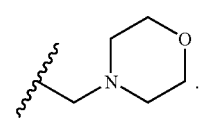

10. A compound having a structure according to formula (II)

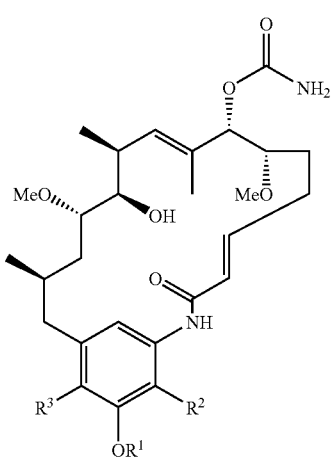

(II)

or a pharmaceutically acceptable salt thereof,
wherein
- $R^1$ is H, optionally substituted $C_1$-$C_5$ alkyl, optionally substituted $C_2$-$C_5$ alkenyl, optionally substituted $C_2$-$C_5$ alkynyl, optionally substituted $C_3$-$C_6$ cycloalkyl, $(CH_2)2C(O)R^7$, $CH_2C(=O)R^7$, or $C(=O)R^8$;
- $R^2$ and $R^3$ are independently H, halogen, optionally substituted $C_1$-$C_5$ alkyl, optionally substituted $C_2$-$C_5$ alkenyl, optionally substituted $C_2$-$C_5$ alkynyl, optionally substituted $C_3$-$C_6$ cycloalkyl, NO, NO2, or $N(R^8R^9)$;
- $R^7$ is H, OH, optionally substituted $C_1$-$C_5$ alkyl, optionally substituted $C_2$-$C_5$ alkenyl, optionally substituted $C_2$-$C_5$ alkynyl, optionally substituted $C_3$-$C_6$ cycloalkyl, $OR^8$, or $N(R^8R^9)$;
- each $R^8$ is independently H, optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl; and
- each $R^9$ is independently H, optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl; or $R^8$ and $R^9$ form, in combination with the nitrogen atom to which they are commonly attached, a 3, 4, 5, or 6 membered heterocyclic ring containing 1, 2, or 3 heteroatoms selected from N, O, and S;

wherein an optionally substituted $C_1$-$C_5$ alkyl, optionally substituted $C_2$-$C_5$ alkenyl, optionally substituted $C_2$-$C_5$ alkynyl, or optionally substituted $C_3$-$C_6$ cycloalkyl that is substituted contains a substituent selected from the group consisting of alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino ciuartemary ammonium, aralkylamino, cycloalkylamino, heterocycloamino, dialkylamino, alkanoylamino, thio, alkylthio, cycloalkylthio, heterocyclothio, ureido, nitro, cyano, carboxy, carboxylalkyl, carbamyl, alkoxycarbonyl, alkylthiono, arylthiono, alkylsulfonyl, sulfonamido, and aryloxy.

11. A compound according to claim 10, wherein each of $R^2$ and $R^3$ is H and $R^1$ is other than H.

12. A compound according to claim 10, wherein $R^1$ is H and at least one of $R^2$ and $R^3$ is other than H.

13. A compound according to claim 10, wherein $R^1$ is optionally substituted $C_1$-$C_5$ alkyl, optionally substituted $C_2$-$C_5$ alkenyl, or $CH_2C(=O)R^7$ and each of $R^2$ and $R^3$ is H.

14. A compound according to claim 13, wherein $R^1$ is

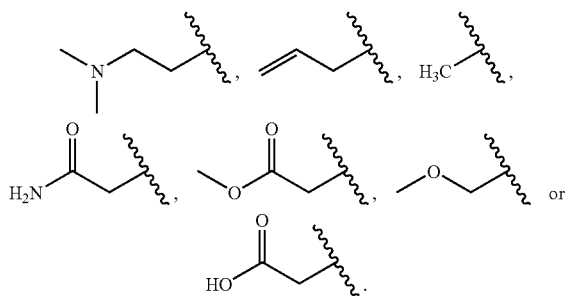

15. A compound according to claim 10, wherein at least one of $R^2$ and $R^3$ is Br or an amino-substituted methylene group.

16. A compound according to claim 15, wherein the amino-substituted methylene group is

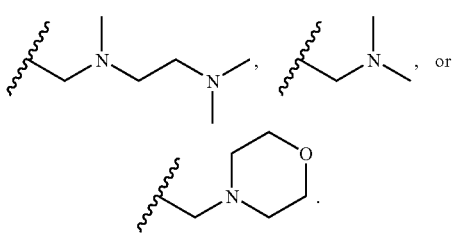

17. A compound according to claim 1, wherein $R^4$ is O.

18. A compound according to claim 10, wherein $R^1$, $R^2$, and $R^3$ are selected from the combinations set forth in the table below:

| $R^1$ | $R^2$ | $R^3$ |
|---|---|---|
| H | H | H |
|  | H | H |
|  | H | H |
| Me | | |

-continued

| R¹ | R² | R³ |
|---|---|---|
| H₂N−C(=O)−CH₂−⁓ | H | H |
| H | (CH₃)₂N−CH₂−⁓ | H |
| H | morpholino-CH₂−⁓ | H |
| CH₃O−C(=O)−CH₂−⁓ | H | H |
| HO−C(=O)−CH₂−⁓ | H | H |
| H | Br | H |
| H | H | Br |
| CH₃O−CH₂−⁓ | H | H |
| H | Br | Br |
| H | Br | ⁓−N(CH₃)−CH₂CH₂−N(CH₃)₂ |
| H | ⁓−N(CH₃)−CH₂CH₂−N(CH₃)−CH₂CH₂−N(CH₃)−⁓ | |
| H | ⁓−N(CH₃)−CH₂CH₂−N(CH₃)₂ | H. |

19. A compound having a structure according to the formula 1-A

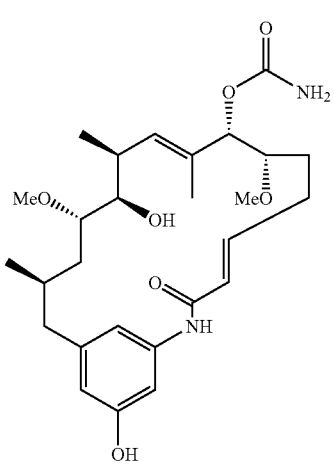

or a pharmaceutically acceptable salt thereof.

20. A compound having a structure according to formula III

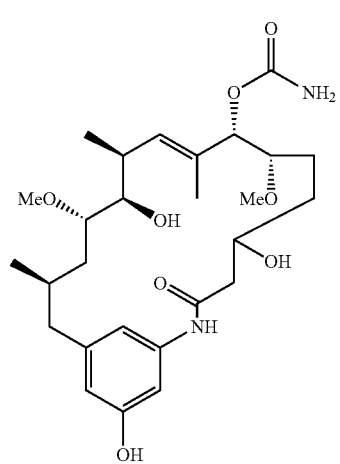

or a pharmaceutically acceptable salt thereof.

21. A compound having a structure according to formula IV

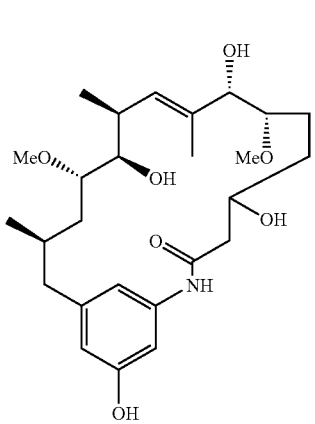

or a pharmaceutically acceptable salt thereof.

22. A method of treating breast cancer, comprising administering to a patient suffering from breast cancer a therapeutically effective amount of a compound according claim 1.

23. A method of treating breast cancer, comprising administering to a patient suffering from breast cancer a therapeutically effective amount of a compound according claim 10.

24. A method of treating breast cancer, comprising administering to a patient suffering from breast cancer a therapeutically effective amount of a compound according claim 19.

25. A method of treating breast cancer, comprising administering to a patient suffering from breast cancer a therapeutically effective amount of a compound according claim 20.

26. A method of treating breast cancer, comprising administering to a patient suffering from breast cancer a therapeutically effective amount of a compound according claim 21.

27. A pharmaceutical formulation comprising a compound according to claim 1 and an excipient.

28. A pharmaceutical formulation comprising a compound according to claim 10 and an excipient.

29. A method of treating leukemia, comprising administering to a patient suffering from leukemia a therapeutically effective amount of a compound according to claim 19.

* * * * *